United States Patent [19] [11] 4,325,842
Slaugh et al. [45] Apr. 20, 1982

[54] PROCESS FOR PREPARING A SUPPORTED MOLYBDENUM CARBIDE COMPOSITION

[75] Inventors: Lynn H. Slaugh; Ronald J. Hoxmeier, both of Houston, Tex.

[73] Assignee: Shell Oil Company, Houston, Tex.

[21] Appl. No.: 213,969

[22] Filed: Dec. 8, 1980

[51] Int. Cl.$^3$ .................. B01J 23/28; B01J 27/22
[52] U.S. Cl. ................................................. 252/443
[58] Field of Search ........................................ 252/443

[56] References Cited

U.S. PATENT DOCUMENTS 4,073,866 10/1976 Yamaki et al. .................. 252/443 X Primary Examiner—W. J. Shine

[57] ABSTRACT

A process for preparing a supported molybdenum carbide composition which comprises impregnating a porous support with a solution of hexamolybdenum dodecachloride, drying the impregnated support and then heating in a carbiding atmosphere at a temperature of about 650°–750° C.

7 Claims, No Drawings

PROCESS FOR PREPARING A SUPPORTED MOLYBDENUM CARBIDE COMPOSITION

FIELD OF THE INVENTION

This invention relates to a process for preparing supported molybdenum carbide compositions useful as catalysts.

BACKGROUND OF THE INVENTION

Transition metal carbides are intriguing materials, some of which have been of industrial interest for a hundred years. It is surprising that the catalytic properties of these materials have been so relatively little investigated. These compounds possess attributes which suggest that they should be valuable catalysts. One would anticipate catalytic activity, since for example carbides behave as metals with the properties enhanced by the addition of carbon. They are electrical conductors and their high degree of chemical inertness should allow them to be used as catalysts under hostile conditions. They have unusually high thermal stabilities and one should be able to use them at very high temperatures without catalyst deactivation due to sintering. The relatively small amount of investigative work performed on the molybdenum carbide for use as catalysts has been performed on bulk materials. Activities have typically been low. It might be expected that if molybdenum carbide were to be supported on a high surface area support, much more interesting catalytic properties would be observed. However, the high temperature reduction conditions that are required to convert say molybdenum oxide to molybdenum carbide also adversely affect the surface area of the underlying support. Thus, a method that would provide for a supported molybdenum carbide catalyst which would retain high surface areas would be very useful in the catalytic arts.

SUMMARY OF THE INVENTION

The instant process provides for a method for preparing supported molybdenum carbide compositions which retain a significant proportion of the surface area of the underlying support. These high surface area supported materials are useful as catalysts. Basically, the method comprises impregnating a porous inert support with a solution of hexamolybdenum dodecachloride dissolved in an organic solvent, heating the impregnated support in a non-oxidizing atmosphere to remove the solvent and subsequently heating to about 650°–750° C. in a carbiding gas mixture comprising hydrogen, lower alkane, alkene or carbon monoxide and a noble gas. The instant process is a relatively mild process which retains a substantial amount of the surface area of the underlying support. The instant process, for example, by using the chloride prepares catalysts having higher surface areas than catalysts using comparable methods but utilizing an oxidic molybdenum compound.

DESCRIPTION OF THE ILLUSTRATIVE EMBODIMENTS

The hexamolybdenum dodecachloride compound used in the instant invention is a hexanuclear cluster compound having the formula $Mo_6Cl_{12}$ and includes the hydrated form $(H_3O)_2Mo_6Cl_{14}\cdot 2H_2O$. This material typically can be prepared, isolated and purified according to the procedures of Larsen ("Inorganic Synthesis", 12, 172 (1970)).

The supports utilized in the preparation of the compositions of this invention are in their broadest aspects selected from the large number of conventional, porous, refractory catalyst carriers or support materials. These materials should not degrade substantially when subjected to the composition preparative techniques of the instant invention. They should not, for example, react with the impregnating solvent nor substantially sinter when heated to the carbiding temperature nor react substantially with the carbiding gas. When the supported materials are used as catalysts it is important that the catalyst support also be essentially inert to the reactant products and reactant conditions. Such conventional support materials may be of natural or synthetic origin. Very suitable supports comprise those of aluminous, siliceous or carbonaceous composition. Specific examples of suitable supports are aluminum oxide, charcoal, graphite, pumice, magnesia, zirconia, kieselguhr, silica, silicaalumina, selected clays, artificial and natural zeolites and ceramics. Refractory supports particularly useful in the preparation of the composition of this invention comprise the aluminas, aluminous materials and the carbonaceous materials. Gamma alumina and activated carbon are particularly useful. The supports may be shaped into particles, chunks, pieces, pellets, rings, spheres, and the like. Prior to use the catalyst support materials are typically calcined at sufficiently high temperatures to remove free water. These conditions of calcination will depend on the particular material involved.

In order to impregnate the support material a solution of hexanuclear molybdenum chloride is prepared by dissolving the hexamolybdenum compound $(H_3O)_2Mo_6Cl_{14}\cdot 2H_2O$ in a suitable organic solvent. The organic solvent is preferably a polar organic solvent, and is most preferably an oxygenated polar organic solvent such as for example an alcohol, an ether, a ketone, a sulfone and the like. Particularly useful solvents are the alcohols, for example the lower alkanols of carbon numbers from 1 to about 6. Ethanol is a particularly desirable solvent. The actual impregnation techniques utilized are conventional in the catalytic art and for example include the so-called dry-impregnation wherein sufficient amount of liquid is utilized to just wet a catalyst support material. Other methods would include the use of excess liquid material, with subsequent removal of this excess by, for example, centrifugation.

After impregnation the impregnated material is dried in order to remove the solvent. The drying conditions must be such that the hexamolybdenum chloride material is not oxidized. At lower temperatures, say up to 150°–200° C., drying may take place in air as for example with the utilization of a vacuum drying oven or by flowing hot dry gas over the material. Above about 150°–200° C. the drying must be carried out in an inert atmosphere in order to prevent the oxidation of the molybdenum chloride. At the higher temperatures the noble gases such as, for example, argon, provide very suitable drying gases. Utilizing these gases, one can dry at temperatures up to about 500° C. although higher temperatures can be used.

After drying the impregnated material is heated at a temperature ranging from about 650° C. to about 750° C. in a carbiding gas. The time at this temperature will be dependent on the temperature utilized. Higher temperature will require shorter time and vice versa. At a given temperature the appropriate time is readily determined by routine experimentation and analysis. Typically the time will range from about 0.1 to about 10 hours and must be sufficient to convert substantially all of these hexamolybdenum chlorides into molybdenum carbides.

The carbiding gas comprises basically hydrogen and a carbiding component with the balance being a noble gas. The concentration of hydrogen will range from about 1 to about 20% by volume. The concentration of the carbiding component will range from about 0.5 to about 5% by volume (gaseous state). The carbiding component will be selected from the group consisting of lower alkane, lower alkene, carbon monoxide and mixtures thereof. The carbon numbers of the lower alkanes and alkenes utilized range from about 1 to about 3. Thus, methane, ethane, propane, ethylene, and propylene, are utilized. Methane is a preferred gas. The noble gases used to dilute the hydrogen and alkane or alkene mixtures are selected from VIIIA of the periodic table and include helium, neon, argon, krypton and xenon. Argon is a preferred noble gas to be utilized.

DESCRIPTION OF THE ILLUSTRATIVE EMBODIMENTS

Synthesis of $(H_3O)_2Mo_6Cl_{14}.2H_2O$

This material was prepared, isolated, and purified according to M. L. Larsen, "Inorganic Synthesis", 12, 172 (1970).

Synthesis of Supported $Mo_2C$ on $Al_2O_3$ from $Mo_6Cl_{12}$

In a typical preparation, Kaiser KA-201 $Al_2O_3$ (Surface Area (SA)=256 m$^2$/g) was calculated 4 hours at 600° C. under an Ar stream. Then a solution of 6.6 g of $(H_3O)_2Mo_6Cl_{14}.2H_2O$ in 28 ml of ethanol was used to dry-impregnate 30 g of $Al_2O_3$ to a 10% by weight Mo loading. This material was dried in a vacuum over at 150° C. for 1 hour then calcined under Ar at 200° C. for 1 hour, 300° C. for 1 hour and 400° C. for 1 hour to give $Mo_6Cl_{12}/Al_2O_3$. The $Mo_6Cl_{12}/Al_2O_3$ was carbided with 90% Ar/8% $H_2$/2% $CH_4$ for 1 hour at 500° C. then for 17 hours at 700° C. After carbiding, the $Al_2O_3$ had SA=190 m$^2$/g.

Synthesis of Supported $Mo_2C$ on Active Carbon from $Mo_6Cl_{12}$

In a typical preparation, active carbon chips (1 mm diameter; a Union Carbide product made via polystyrene pyrolysis—SA=1200 m$^2$/g) were calcined for 1 hour at 700° C. under $H_2$ before use. Then a solution of 3.3 g $(H_3O)_2Mo_6Cl_{14}.2H_2O$ in 30 ml of ethanol was used to dry impregnate 15 g of active carbon to a 10% by weight metal loading. This material was dried in a vacuum oven at 150° C. for 1 hour and then calcined under Ar at 200° C. for 1 hour, 300° C. for 1 hour, and 400° C. for 1 hour to give $Mo_6Cl_{12}/C$. The $Mo_6Cl_{12}/C$ was carbided with 90% Ar/8% $H_2$/2% $CH_4$ for 1 hour at 500° C. then for 17 hours at 700° C. After carbiding, the active carbon support had SA=1180 m$^2$/g.

Synthesis of Supported Mo from $Mo_6Cl_{12}$

For comparison purposes catalysts of Mo metal supported on $Al_2O_3$ and active carbon were prepared. The synthesis of Mo supported on $Al_2O_3$ and on active carbon were carried out in exactly the same fashion as for the preparation of the analagous supported $Mo_2C$ with the exception that pure $H_2$ was used as reducing agent rather than the Ar/$H_2$/$CH_4$ gas mixture used for carbiding.

Toluene Cracking and Dealkylation Reactions

To test the catalytic activities of the compositions of the instant invention, the cracking and the de-alkylation of toluene was studied. A high pressure trickle-phase reactor containing 9.2 ml of catalysts was used along with the toluene feed flow rate of 9.2 ml/hr. supplied by a syringe pump. The hydrogen to toluene ratio was 4 to 1, the hydrogen pressure was 375 lbs.; the hydrogen flow rate was 9.0 liters per hour; and the LHSV was 1. Liquid product was collected and weighed and then the product composition determined by GC analysis using an SE-30 column. Gas phase product volume was determined by flow rates to a wet test meter and gas composition determined via a GC-MS analysis.

$Al_2O_3$ Support Catalyst

The data of the reaction for the alumina supported catalysts are presented in Table 1. The reactor temperature for this data was 480° C. At the temperature of this reaction the primary reactions for both the molybdenum metal supporting catalysts and the molybdenum carbide supported catalysts are toluene dealkylation to benzene and cracking to light hydrocarbons. The molybdenum carbide supported catalyst is significantly more active than the molybdenum metal supported catalyst, effecting a 73% conversion of toluene versus a 42% conversion level for molybdenum metal (line 23). The molybdenum carbide supported catalyst is also more selective for benzene production (59% vs. 40% for molybdenum metal supported catalyst-line 18). The appropriate blanks were run on the alumina support alone. At this temperature alumina was found to be completely inactive in converting toluene to benzene or in cracking toluene to light hydrocarbons. Thus, it can be seen that the molybdenum carbide supported compositions are catalytic for the cracking and dehydroalkylation of toluene and are more active and more selective than the molybdenum metal supported catalysts or the support alone.

Active Carbon Supported Catalyst

Data for the dehydroalkylation of toluene on active carbon supported catalysts are presented in Table 2. Unlike the alumina supported catalysts, neither the molybdenum carbide active carbon catalysts nor the molybdenum metal active carbon catalysts showed significant toluene dealkylation activity at 480° C. In fact, reasonable toluene conversions were not observed with these systems until reaction temperatures of 550° C. or higher were employed. On active carbon supports, molybdenum carbide possessed higher toluene dealkylation activity than molybdenum metal (44% conversion vs. 34% for molybdenum metal-line 21). Comparably high selectivities to benzene were observed for both of these catalysts. At 600° C., deep toluene conversion is seen for the molybdenum carbide-active carbon catalyst while retaining still an impressive selectivity to benzene (greater than 95% selectivity to benzene at 70% conversion of toluene-lines 17 and 21 respectively).

Appropriate blanks were run for the active carbon supported materials as well. An empty tube reaction showed that toluene alone is not thermally dealkylated to benzene with hydrogen at 550° C. or at 600° C. However, the active carbon support was found to have significant activity of its own for this reaction. At 550° C., active carbon gave a 27% conversion of toluene with greater than 96% selectivity to benzene (line 21 and line 19, respectively). This accounts for more than half the zene production, the supported molybdenum carbide on active carbon support provides even further enhanced catalytic properties.

TABLE I

| | | 480° C. | | | |
|---|---|---|---|---|---|
| 1. | Temperature | | | | |
| 2. | Catalyst Type | Mo/Al$_2$O$_3$ | | Mo$_2$C/Al$_2$O$_3$ | |
| 3. | Exit Gas (l/hr) | 8.1 | | 8.4 | |
| 4. | Liquid Product (g/hr) | 7.5 | | 5.5 | |
| 5. | Products | mmoles | C$_7$ equivs | mmoles | C$_7$ equivs |
| 6. | CH$_4$ (g)(dealkylation) | 13.5 | 1.9 | 35.3 | 5.0 |
| 7. | CH$_4$ (g)(cracking) | 31.7 | 4.5 | 67.6 | 9.7 |
| 8. | C$_2$H$_6$ (g) | 7.3 | 2.1 | 10.4 | 3.0 |
| 9. | C$_3$H$_8$ (g) | 3.4 | 1.5 | 5.0 | 2.1 |
| 10. | C$_4$H$_{10}$ (g) | 1.8 | 1.0 | 3.0 | 1.7 |
| 11. | C$_5$H$_{12}$ (g) | 1.0 | 0.7 | 1.2 | 0.9 |
| 12. | C$_4$ avg (l)$^a$ | 13.4 | 7.7 | 9.2 | 5.2 |
| 13. | Benzene (l + g) | 13.5 | 11.6 | 35.3 | 30.3 |
| 14. | Methylcyclohexane (l + g) | — | — | — | — |
| 15. | Xylenes (l + g) | 2.6 | 3.0 | 2.1 | 2.4 |
| 16. | Toluene (l + g) | 46.2 | 46.2 | 22.2 | 22.2 |
| 17. | Selectivity (%) | | | | |
| 18. | Benzene$^b$ | | 39.7 | | 58.5 |
| 19. | Methylcyclohexane$^b$ | | — | | — |
| 20. | Xylenes$^b$ | | 7.6 | | 3.5 |
| 21. | Cracking$^c$ | | 51.5 | | 37.5 |
| 22. | Materials Balance$^d$ (%) | | 92.7 | | 95.4 |
| 23. | Toluene Conversion$^e$ (%) | | 42.4 | | 73.1 |

$^a$Cracked products in liquid phase assumed to have average M.W. = C$_4$H$_{10}$.

$^b$Selectivity = $\dfrac{\text{mmoles product}}{\text{C}_7 \text{ equivalents of all products}} \times 100$.

$^c$Selectivity = $\dfrac{\text{C}_7 \text{ equivalents of cracked products}}{\text{C}_7 \text{ equivalents of all products}} \times 100$.

$^d$Materials Balance = $\dfrac{\text{C}_7 \text{ equivalents of products} + \text{C}_7 \text{ equivalents of unconverted toluene}}{\text{mmoles toluene feed}} \times 100$.

$^e$Toluene Conversion = $\dfrac{\text{C}_7 \text{ equivalents of products}}{\text{C}_7 \text{ equivalents of products} + \text{C}_7 \text{ equivalents of unconverted toluene}} \times 100$.

Note: g and l in lines 6–16 refer to "gas" and "liquid", respectively.

TABLE II

| | | 550° C. | | | | | | 600° C. | | | |
|---|---|---|---|---|---|---|---|---|---|---|---|
| 1. | Temperature | | | | | | | | | | |
| 2. | Catalysts Type | Active C | | Mo/active C | | Mo$_2$C/active C | | Active C | | Mo$_2$C/active C | |
| 3. | Exit Gas (l/hr) | 9.9 | | 9.5 | | 9.1 | | 11.4 | | 9.7 | |
| 4. | Liquid Product (g/hr) | 7.4 | | 7.1 | | 7.4 | | 6.9 | | 6.6 | |
| 5. | Products | mmoles | C$_7$ equivs | mmoles | C$_7$ equivs | mmoles | C$_7$ equivs | mmoles | C$_7$ equivs | mmoles | C$_7$ equivs |
| 6. | CH$_4$ (g)(dealkylation) | 18.9 | 2.7 | 23.8 | 3.4 | 30.1 | 4.3 | 41.7 | 6.0 | 55.4 | 7.9 |
| 7. | CH$_4$ (g)(cracking) | — | — | — | — | — | — | — | — | 4.4 | 0.6 |
| 8. | C$_2$H$_6$ (g) | 0.3 | 0.1 | 0.4 | 0.1 | 1.3 | 0.4 | 1.0 | 0.3 | 2.6 | 0.7 |
| 9. | C$_3$H$_8$ (g) | 0.2 | 0.1 | 0.2 | 0.1 | 0.6 | 0.3 | 0.2 | 0.1 | 0.8 | 0.3 |
| 10. | C$_4$H$_{10}$ (g) | — | — | — | — | 0.3 | 0.2 | — | — | 0.1 | 0.1 |
| 11. | C$_5$H$_{12}$ (g) | — | — | — | — | 0.1 | 0.1 | — | — | 0.2 | 0.1 |
| 12. | C$_4$ ave (l)$^a$ | — | — | 0.2 | 0.1 | 1.4 | 0.8 | — | — | 0.5 | 0.3 |
| 13. | Benzene (l + g) | 21.8 | 18.7 | 27.1 | 23.2 | 35.5 | 30.4 | 42.1 | 36.1 | 55.4 | 47.5 |
| 14. | Xylenes (l + g) | 0.8 | 0.9 | 0.7 | 0.8 | 1.0 | 1.1 | 1.2 | 1.4 | 0.5 | 0.6 |
| 15. | Toluene (l + g) | 62.2 | 62.2 | 54.0 | 54.0 | 48.8 | 48.8 | 39.6 | 39.6 | 25.2 | 25.2 |
| 16. | Selectivity (%)$^b$ | | | | | | | | | | |
| 17. | Benzene | 96.8 | | 97.8 | | 94.4 | | 95.9 | | 95.4 | |
| 18. | Xylenes | 3.5 | | 2.5 | | 2.7 | | 3.2 | | 0.9 | |
| 19. | Cracking | 0.9 | | 1.1 | | 4.9 | | 0.9 | | 3.6 | |
| 20. | Materials Balance (%)$^b$ | 97.4 | | 94.3 | | 99.9 | | 96.0 | | 96.3 | |
| 21. | Toluene Conversion (%)$^b$ | 26.6 | | 33.9 | | 43.5 | | 52.6 | | 69.7 | |

$^a$Cracked products in liquid phase assumed to have average M.W. = C$_4$H$_{10}$.
$^b$Calculated as in Table 1.
Note: g and l in lines 6–15 refer to "gas" and "liquid", respectively.

activities seen for the molybdenum metal and the molybdenum carbide catalysts at this temperature. At 600° C. the active carbon catalyst yield at 53% conversion of toluene with selectivity to benzene still greater than 95% (lines 21 and 17, respectively). This accounts for about 75% of the activities seen for the molybdenum carbide catalyst under the same conditions. Thus, although active carbon itself is a very effective and highly selective toluene hydrodealkylation catalysts for ben-

What is claimed is:

1. A process for preparing a supported molybdenum carbide composition which comprises impregnating a porous, inert support with a solution of (H$_3$O)$_2$Mo$_6$Cl$_{14}$·2H$_2$O dissolved in an organic solvent, heating the impregnated support under non-oxidizing conditions in order to remove the solvent and subsequently heating the impregnated support to a temperature ranging from about 650° C. to about 750° C. in a carbidng gas mixture which comprises hydrogen in a concentration ranging from about 1 to about 20 percent by volume, a carbiding component selected from the group consisting of lower alkane, lower alkene, carbon monoxide and mixtures thereof in a concentration ranging from about 0.5 to about 5 percent by volume and the balance being a noble gas.

2. The process of claim 1 wherein the solvent is a polar organic solvent.

3. The process of claim 2 wherein the solvent is an oxygenated solvent.

4. The process of claim 3 wherein the solvent is selected from the group consisting of alcohols, ethers and ketones.

5. The process of claim 4 wherein the solvent is a lower alcohol having a carbon number ranging from about 1 to about 6.

6. The process of claim 1 wherein the alkane and/or alkene is selected from the group consisting of methane, ethane, propane, ethylene, and propylene.

7. The process of claim 6 wherein the alkane is methane.

* * * * *